(12) United States Patent
Brannan (10) Patent No.: US 10,085,801 B2
(45) Date of Patent: Oct. 2, 2018

(54) SYSTEMS AND METHODS FOR USING A DIGITAL CONTROLLER TO ADJUST ONE OR MORE OPERATIONS OF A MICROWAVE GENERATOR

(71) Applicant: COVIDIEN LP, Mansfield, MA (US)

(72) Inventor: Joseph D. Brannan, Erie, CO (US)

(73) Assignee: Covidien LP, Mansfiled, MA (US)

( * ) Notice: Subject to any disclaimer, the term of this patent is extended or adjusted under 35 U.S.C. 154(b) by 470 days.

(21) Appl. No.: 14/805,084

(22) Filed: Jul. 21, 2015

(65) Prior Publication Data

US 2016/0051326 A1    Feb. 25, 2016

Related U.S. Application Data

(60) Provisional application No. 62/041,402, filed on Aug. 25, 2014.

(51) Int. Cl.
*A61B 18/18* (2006.01)
*A61B 19/00* (2006.01)
(Continued)

(52) U.S. Cl.
CPC .......... *A61B 18/1815* (2013.01); *A61B 19/44* (2013.01); *A61B 90/98* (2016.02);
(Continued)

(58) Field of Classification Search
CPC .................... A61B 18/18; A61B 18/15; A61B 2018/00577; A61B 2018/00642;
(Continued)

(56) References Cited

U.S. PATENT DOCUMENTS

| 4,739,759 A | 4/1988 | Rexroth et al. |
| 5,599,344 A | 2/1997 | Paterson |

(Continued)

FOREIGN PATENT DOCUMENTS

| AU | 2008202726 A1 | 1/2009 |
| CN | 2631444 Y | 8/2004 |
| CN | 103006320 A | 4/2013 |

OTHER PUBLICATIONS

Extended European Search Report issued in Patent Application No. 15835466.2 dated May 23, 2018.

(Continued)

*Primary Examiner* — Thomas Giuliani (57) ABSTRACT

A surgical system is presented including a microwave generator having a resistive identification connector with a plurality of resistive channels, each resistive channel having a plurality of resistive values. The surgical system further includes a microwave applicator having a device identifier, the microwave applicator configured to be connected to the microwave generator via a reusable cable. The surgical system also includes a digital controller configured to be connected to the resistive identification connector of the microwave generator. The device identifier of the microwave applicator is relayed to the digital controller via a resistive channel of the plurality of resistive channels of the resistive identification connector to enable the digital controller to control the microwave applicator by adjusting at least one operation of the microwave generator. The microwave generator further includes at least one digital pass-through line to allow direct communication between the microwave applicator and the digital controller.

10 Claims, 3 Drawing Sheets

(51) Int. Cl.
*A61B 90/98* (2016.01)
*A61B 18/00* (2006.01)
*A61B 17/00* (2006.01)

(52) U.S. Cl.
CPC ........... *A61B 2017/00482* (2013.01); *A61B 2018/00178* (2013.01); *A61B 2018/00577* (2013.01); *A61B 2018/00642* (2013.01); *A61B 2018/00678* (2013.01); *A61B 2018/00779* (2013.01); *A61B 2018/00785* (2013.01); *A61B 2018/00791* (2013.01); *A61B 2018/00886* (2013.01); *A61B 2018/00988* (2013.01); *A61B 2018/1823* (2013.01); *A61B 2019/448* (2013.01)

(58) Field of Classification Search
CPC .... A61B 2018/1823; A61B 2018/1861; A61B 2018/00178; A61B 2018/00785; A61B 2018/00678; A61B 2018/00779; A61B 2018/00988; A61B 90/98; A61B 2090/0803; A61B 2090/0814; A61B 2017/00119; A61B 18/1233; A61B 18/1206; A61B 2018/00958
USPC .................................. 606/33; 607/101, 156
See application file for complete search history.

(56) References Cited

U.S. PATENT DOCUMENTS

| | | | |
|---|---|---|---|
| 5,633,578 A | 5/1997 | Eggers et al. | |
| 6,033,399 A | 3/2000 | Gines | |
| 6,165,169 A * | 12/2000 | Panescu ............. | A61B 18/1492 606/1 |
| 6,383,183 B1 * | 5/2002 | Sekino ............... | A61B 18/1206 606/34 |
| 7,909,820 B2 | 3/2011 | Lipson et al. | |
| 8,430,874 B2 | 4/2013 | Newton et al. | |
| 8,562,598 B2 | 10/2013 | Falkenstein et al. | |
| 8,623,007 B2 | 1/2014 | Deborski et al. | |
| 8,652,125 B2 | 2/2014 | Keller | |
| 8,915,910 B2 | 12/2014 | Falkenstein et al. | |
| 2003/0176856 A1 * | 9/2003 | Howell ................. | A61B 18/08 606/29 |
| 2005/0137654 A1 * | 6/2005 | Hoenig ................. | A61N 5/04 607/86 |
| 2010/0324548 A1 * | 12/2010 | Godara ............. | A61B 18/1492 606/34 |
| 2011/0118723 A1 * | 5/2011 | Turner ............... | A61B 18/1815 606/33 |
| 2013/0267945 A1 | 10/2013 | Behnke, II et al. | |
| 2014/0066927 A1 | 3/2014 | Brustad et al. | |

OTHER PUBLICATIONS

First Office Action issued by the Chinese Patent Office in Application No. 201580045552.7, dated Jul. 26, 2018.

* cited by examiner

SYSTEMS AND METHODS FOR USING A DIGITAL CONTROLLER TO ADJUST ONE OR MORE OPERATIONS OF A MICROWAVE GENERATOR

CROSS REFERENCE TO RELATED APPLICATION

This application claims the benefit of and priority to U.S. Provisional Patent Application No. 62/041,402 filed Aug. 25, 2014, the entire contents of which are hereby incorporated by reference.

BACKGROUND

1. Technical Field

The present disclosure relates to microwave generators and, more particularly, to systems and methods for using a digital controller to adjust one or more operations of a microwave generator.

2. Discussion of Related Art

Electromagnetic fields can be used to heat and destroy tumor cells. Treatment may involve inserting ablation probes into tissues where cancerous tumors have been identified. Once the ablation probes are properly positioned, the ablation probes induce electromagnetic fields within the tissue surrounding the ablation probes.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic fields to heat or ablate tissue.

Devices utilizing electromagnetic fields have been developed for a variety of uses and applications. Typically, apparatuses for use in ablation procedures include a power generation source, e.g., a microwave generator that functions as an energy source, and a surgical instrument (e.g., microwave ablation probe having an antenna assembly) for directing energy to the target tissue. The generator and surgical instrument are typically operatively coupled by a cable assembly having a plurality of conductors for transmitting energy from the generator to the instrument, and for communicating control, feedback, and identification signals between the instrument and the generator.

There are several types of microwave probes and waveguides in use, e.g., monopole, dipole, and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly-aligned and positioned end-to-end relative to one another with an electrical insulator placed therebetween. Helical antenna assemblies include helically-shaped conductor configurations of various dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

The heating of tissue for thermal ablation is accomplished through a variety of approaches, including conduction of heat from an applied surface or element, ionic agitation by electrical current flowing from an electrode to a ground pad, optical wavelength absorption, or, in the case of microwave ablation, by dielectric relaxation of water molecules within an applied electromagnetic field. Regardless of the approach, conceptually thermally ablative devices coagulate and necrose tissue with two distinct heating zones; an active heating zone and a passive heating zone.

The active ablation zone is closest to the ablation device and encompasses the volume of tissue which is subjected to energy absorption high enough to assure thermal tissue destruction at a given application time in all but areas of very rapidly flowing fluids, such as around and within large blood vessels or airways. The active ablation zone size and shape is determined by ablation device design. The active ablation zone can therefore be used to produce predictable ablative effects over a given shape and volume of tissue.

The passive ablation zone surrounds the active zone and encompasses the volume of tissue which experiences a lower intensity of energy absorption. The tissue within the passive ablation zone may or may not experience tissue destruction at a given application time. Physiological cooling may counter heating from the lower level energy absorption and therefore not allow for sufficient heating to occur within the passive zone to kill tissue. Diseased or poorly perfused tissue within the passive zone may be more prone to heating than other tissues and may also be more susceptible to heat conduction from hotter areas within the ablation zone. The passive zone in these cases can result in unexpectedly large ablation zones. Due to these varying scenarios across space within a targeted physiology, relying on the passive zone to perform thermal ablation is challenging with unpredictable outcomes.

As electromagnetic fields can be induced at a distance by microwave probes, microwave ablation has the potential to create large active zones whose shapes can be determined and held constant by design. Furthermore, the shape and size can be determined through design to fit a specific medical application. By utilizing a predetermined active zone to create a predictable ablation zone, and not relying upon the indeterminate passive ablation zone, microwave ablation can provide a level of predictability and procedural relevance not possible with other ablative techniques.

The shape of the active zone about an antenna is determined by the frequency of operation, the geometry of the antenna, the materials of the antenna, and the medium surrounding the antenna. Operating an antenna in a medium of dynamically changing electrical properties, such as heating tissue, results in a changing shape of the electromagnetic field, and therefore a changing shape of the active zone. To maintain the shape of the active zone about a microwave antenna, the degree of influence on the electromagnetic field of the surrounding medium's electrical properties is reduced.

The size of the active zone about an antenna is determined by the amount of energy which can be delivered from the microwave generator to the antenna. With more energy delivered to the antenna, larger active zones can be generated. To maximize energy transfer from a microwave generator through waveguides and to a microwave antenna requires each system component to have the same impedance, or to be impedance matched. Whereas the impedance of the generator and waveguides are typically fixed, the impedance of a microwave antenna is determined by the frequency of operation, the geometry of the antenna, the materials of the antenna, and the medium surrounding the antenna. Operating an antenna in a medium of dynamically changing electrical properties, such as within heating tissue, results in a changing antenna impedance and varied energy delivery to the antenna, and, as a result, a changing size of the active zone. To maintain the size of the active zone about a microwave antenna, the degree of influence on the antenna impedance of the surrounding medium's electrical properties must be reduced.

In microwave ablation, the primary cause of active zone size and shape change is an elongation of the electromagnetic wave. Wavelength elongation occurs in heating tissue due to tissue dehydration. Dehydration reduces the dielectric constant of tissue about the probe, elongating the wavelength of microwave fields. Wavelength elongation is also encountered when a microwave device is used across various tissue types due to the varying dielectric constant between tissue types. For example, an electromagnetic wave is significantly longer in lung tissue than in liver tissue.

Wavelength elongation compromises the focus of microwave energy on the targeted tissue. With large volume ablation, a generally spherical active zone is preferable to focus the energy on generally spherical tissue targets. Wavelength elongation causes the electromagnetic field to stretch down along the length of the device toward the generator, resulting in a generally comet- or "hot-dog"-shaped active zone.

Wavelength elongation can be significantly reduced in medical microwave antennas by dielectrically buffering the antenna geometry with a material having an unchanging dielectric constant, as described in U.S. application Ser. Nos. 13/835,283 and 13/836,519, the disclosure of each of which are incorporated by reference herein. The material of unchanging dielectric constant surrounds the antenna, reducing the influence of the tissue electrical properties on antenna wavelength. By controlling wavelength elongation through dielectric buffering, the antenna impedance match and field shape can be maintained, enabling a large active ablation zone with a predetermined and robust shape.

By providing dielectric buffering with a circulated fluid, such as with saline or water, the high dielectric constants of these materials can be leveraged in the antenna geometry design, and furthermore the circulated fluid can be used to simultaneously cool the microwave components, including the coaxial feed line and antenna. Cooling of the microwave components also enables higher power handling of the components which can be used to deliver more energy to the antenna to create larger active zones.

Some microwave generators currently on the market have been developed and refined so that no digital circuitry is required for control. Instead, all functions of the device are controlled by analog control systems. This includes the reflective power measurements, the amplifier control circuitry and others. Indeed, in some instances the only digital aspects of these microwave generators or related to the digital display of the timer and or the power setting.

However, microwave surgical instruments are constantly upgraded with new functions that may not be compatible with these existing electrosurgical generators. However, reprogramming or upgrading an electrosurgical generator for the purpose of interacting with new microwave surgical instruments is cumbersome and has its own drawbacks. According there is a need for a system and method of adding or altering or adjusting operations or functionality of existing microwave generators.

SUMMARY

In an aspect of the present disclosure, a surgical system is presented including a microwave generator having a resistive identification connector including a plurality of resistive channels, each resistive channel having a plurality of resistive values. The surgical system further includes a microwave applicator having a device identifier, the microwave applicator configured to be connected to the microwave generator via a reusable cable. The surgical system also includes a digital controller configured to be connected to the resistive identification connector of the microwave generator. The device identifier of the microwave applicator is relayed to the digital controller via a resistive channel of the plurality of resistive channels of the resistive identification connector to enable the digital controller to control the microwave applicator by adjusting at least one operation of the microwave generator.

In some aspects, the device identifier includes information related to at least one of a power limit, a time limit, a temperature limit, and a reflected power limit of the microwave applicator.

In certain aspects, the plurality of resistive channels are five channels, each of the five channels configured to correspond to a different microwave applicator connected to the microwave generator.

In aspects, a radiometry detector may be connected between the microwave generator and the reusable cable. The radiometry detector senses emissions from tissue in proximity of the microwave applicator.

In some aspects, a footswitch may be connected to the microwave generator. Moreover, a remote temperature probe may be connected to the microwave generator.

In another aspect of the present disclosure, a plurality of dip switches are incorporated onto the microwave generator, the plurality of dip switches configured to allow for high temperature cutoff selectability.

In aspects, the digital controller reads information stored in the device identifier of the microwave applicator to continuously, and in real-time, adjust the at least one operation of the microwave generator.

In some aspects, the microwave generator includes at least one digital pass-through line to allow direct communication between the microwave applicator and the digital controller.

In still other aspects of the present disclosure, a method for operating a microwave applicator is presented. The method includes the steps of connecting the microwave applicator to a microwave generator, via a reusable cable, the microwave generator including a resistive identification connector having a plurality of resistive channels, each resistive channel having a plurality of resistive values, associating the microwave applicator with a device identifier, and connecting a digital controller to the resistive identification connector of the microwave generator. The method further includes the steps of relaying the device identifier of the microwave applicator to the digital controller via a resistive channel of the plurality of resistive channels of the resistive identification connector and enabling the digital controller to control the microwave applicator by adjusting at least one operation of the microwave generator.

Further scope of applicability of the present disclosure will become apparent from the detailed description given hereinafter. However, it should be understood that the detailed description and specific examples, while indicating illustrative embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

Various aspects of the present disclosure are described hereinbelow with reference to the drawings, wherein.

The figures depict illustrative embodiments of the present disclosure and are not intended to be exhaustive. One skilled in the art will readily recognize from the following detailed description that alternative embodiments of the structures and methods illustrated herein may be employed without departing from the principles of the present disclosure.

DETAILED DESCRIPTION

The present disclosure is generally directed to adding digital outputs to a microwave generator that is configured to communicate with a digital controller (or external adapter or dongle), the digital controller configured to adjust one or more operations of the microwave generator in order to manipulate/control a microwave applicator connected to the microwave generator.

One embodiment of the present disclosure is generally directed to providing a microwave generator with resistive identification circuitry configured to operably communicate with the digital controller. When a microwave applicator is connected to the microwave generator, a device ID of the microwave applicator sends or transmits or communicates resistive information associated with the microwave applicator to the resistive identification circuitry, which matches the resistive information with resistive channels to identify the type of microwave applicator attached to the microwave generator. The digital controller is then enabled to be connected to the microwave generator in order to adjust one or more operations of the microwave generator in order to control the microwave applicator connected to the microwave generator.

Embodiments of the microwave ablation systems and components are described with reference to the accompanying drawings. Like reference numerals may refer to similar or identical elements throughout the description of the figures. As shown in the drawings and as used in this description, the term "proximal" refers to that portion of the apparatus, or component of the apparatus, closer to the user and the term "distal" refers to that portion of the apparatus, or component thereof, farther from the user.

Figure 1:
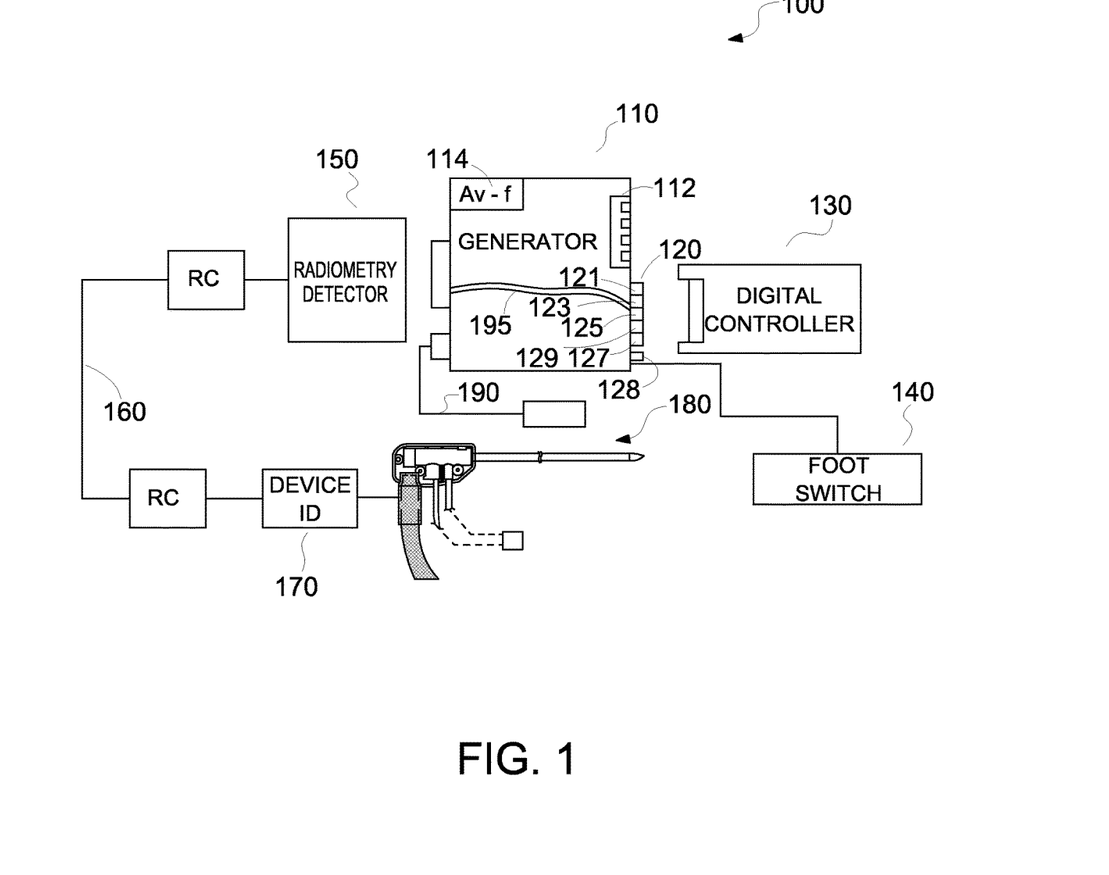
FIG. 1 is a block diagram of a surgical system, in accordance with embodiments of the present disclosure.

FIG. 1 is a block diagram of a surgical system, in accordance with embodiments of the present disclosure. As shown in FIG. 1, the surgical system 100 includes a microwave generator 110. The microwave generator 110 includes a resistive identification connector 120 having a plurality of resistive channels 121, 123, 125, 127, 129, each resistive channel having a plurality of resistive values (see FIG. 2).

The microwave generator 110 is configured to be connected to a microwave applicator 180. The connection between the microwave generator 110 and the microwave applicator 180 is enabled through a reusable cable 160. In one exemplary embodiment, a radiometry detector 150 is positioned between the reusable cable 160 and the microwave generator 110. Moreover, the microwave applicator 180 is associated with a device ID 170 (or device identifier 170). The device ID 170 may be incorporated within the microwave applicator 180 or may be a separate component formed, for example, in a connector configured to mate with a connector of the reusable cable 160. Therefore, the reusable cable 160 connects to the device ID 170, which in turn is connected to the microwave applicator 180. Similar device ID components may be included in the reusable cable 160 and the radiometry detector 150. The microwave generator 110 may also be connected to a footswitch 140, which may also include a device ID.

During the use of the surgical system 100, surgical equipment used when performing surgery and the control of a variety of different subsystems, may be required. Typically, the operation of the subsystems is controlled by a microprocessor-driven console (e.g., the microwave generator 110). The microprocessor receives mechanical inputs from either the operator of the surgical system 100 or from an assistant. A control input device, such as the footswitch 140, is often used to accept mechanical inputs. These mechanical inputs originate from the movement of the foot of an operator to govern the operation of a subsystem within the surgical system 100. The mechanical inputs from the movement of the foot of the operator are translated into electrical signals which are fed to the microprocessor controls. The electrical signals are then used to control the operational characteristics of a subsystem in the surgical system 100.

As shown in FIG. 1, the microwave generator 110 is connected to a remote temperature probe 190. The remote temperature probe 190 may be a temperature sensor such as a thermocouple or a thermistor, and may include a device ID as well. The temperature probe 190 is operable to measure a temperature of tissue at a surgical site. In one embodiment, the temperature probe 190 may be configured to continuously output the temperature signal to the microwave generator 110 allowing a user to observe the temperature or to control the microwave generator 110.

In one embodiment, the dip switches 112, described in greater detail below, enable the setting of a cut-off temperature, and when that temperature is sensed by the remote temperature probe 190, the microwave generator 110 is shut off. As to the monitoring of the temperature, the microwave generator 110 may include a video screen (not shown) that displays the temperature signal output from the temperature probe 190. The display of the temperature signal may be visual (such as a graph or a plurality of colored LEDs), numerical, or otherwise. In other versions, the video screen may be mounted to the microwave applicator 180. Still further, the sensed temperature from the remote temperature probe 190 may be converted to a digital signal and transmitted to digital controller 130, as will be described in greater detail below. The conversion to a digital signal may occur in the microwave generator 110 or in the digital controller 130 without departing from the scope of the present disclosure.

As noted above, the microwave generator 110 is further configured to connect and communicate with a digital controller 130. The digital controller 130 may also be referred to as an external adapter or a dongle. The digital controller 130 is configured to be connected to the resistive identification connector 120 of the microwave generator 110, and one or more analog or digital connectors 128. The resistive identification connector 120 includes a plurality of resistive channels 121, 123, 125, 127, 129. The device identifier 170 of the microwave applicator 180 includes identification information that is associated with one of the resistive channels (e.g., 121) of the plurality of resistive channels 121, 123, 125, 127, 129 of the resistive identification connector 120 to enable the digital controller 130 to receive information regarding the microwave applicator 180, and other components connected to the system 100. This information received via the resistive identification connector 120 enables the controller 130 to execute algorithms to control the microwave generator 110 and the microwave applicator 180.

Figure 2:
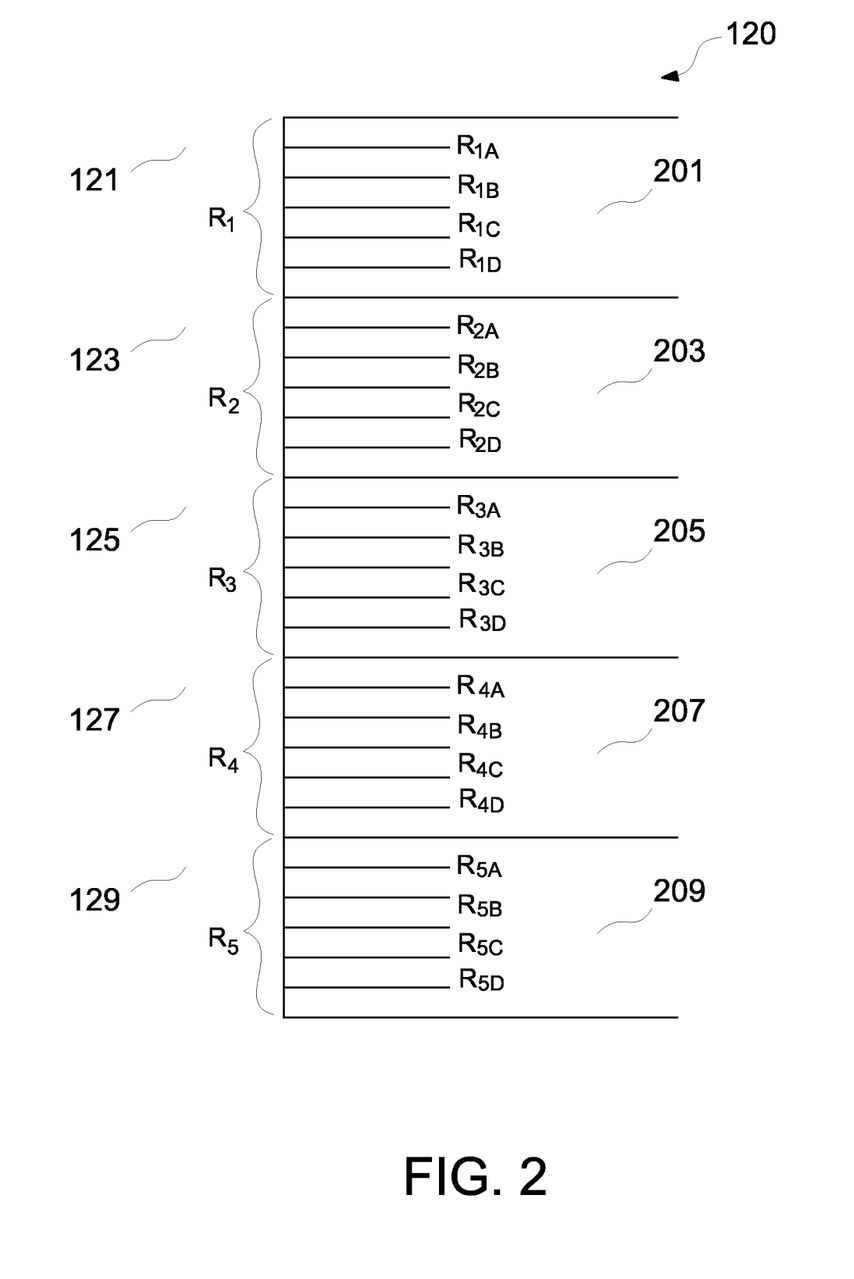
FIG. 2 depicts a resistive identification connector of the surgical system of FIG. 1, in accordance with an embodiment of the present disclosure.

As shown in FIG. 2, the resistive identification connector 120 has a plurality of resistive channels 121, 123, 125, 127, 129, each resistive channel capable of relaying a plurality of resistive values, each of which may relate to a different aspect of the surgical system 100. As an example, the device ID 170 of the microwave applicator 170 transmits or sends or communicates information to the resistive identification connector 120. This information includes at least resistance or resistive values associated with the microwave applicator 180, which can be used to inform the controller 130 of the attributes of the microwave applicator 180, its functional characteristics, how energy is to be applied through the microwave applicator 180, and other features.

The resistive value information is matched with one of the resistive channels 121, 123, 125, 127, 129 of the resistive identification connector 120. For example, the resistive value information of the microwave applicator 180 connected to the microwave generator 110 may correspond to resistive values of the second resistive channel, i.e., channel 123. Once a match of resistances has successfully occurred, the digital controller 130 is capable of determining the type of microwave applicator 180. For example, the microwave applicator 180 may be a single mode applicator, a multi-mode applicator, a needle applicator, a helical applicator, a coil applicator, or some other type of applicator. Once the digital controller 130 identifies the type of microwave applicator attached to the microwave generator 110, the digital controller 130 can control at least one operation of the microwave generator 110.

One or more operations or functions of the microwave generator 110 may be altered or changed or adjusted or manipulated by the digital controller 130. The resistive identification connector 120 of the microwave generator 110 can identify the type of surgical instrument or microwave applicator attached to the microwave generator 110. Thus, identification of the type of microwave applicator occurs by resistance matching of characteristics of the microwave applicator, and other components of the system 100 to the resistance channels 121, 123, 125, 127, 129 of the resistive identification connector 120. In one exemplary embodiment, five resistance or resistive channels may be provided by the resistive identification connector 120. However, one skilled in the art may contemplate using any number of resistive channels. The details of the resistive channels are described below in detail with respect to FIG. 2.

In the exemplary embodiment of FIG. 2, the resistive identification connector 120 includes five channels 121, 123, 125, 127, 129. Each channel includes a plurality of resistive values 201, 203, 205, 207, 209. The resistive value 201 may be a range of resistance values designated as $R_{1A}$, $R_{1B}$, $R_{1C}$, and $R_{1D}$. This range of resistive value 201 may be within, e.g., 0-50 ohms. The resistive value 203 may be a range of resistance values designated as $R_{2A}$, $R_{2B}$, $R_{2C}$, and $R_{2D}$. This range of resistive value 203 may be within, e.g., 0-10 ohms. The resistive value 205 may be a range of resistance values designated as $R_{3A}$, $R_{3B}$, $R_{3C}$, and $R_{3D}$. This range of resistive value 205 may be within, e.g., 10-100 ohms. The resistive value 207 may be a range of resistance values designated as $R_{4A}$, $R_{4B}$, $R_{4C}$, and $R_{4D}$. This range of resistive value 207 may be within, e.g., 100-1000 ohms. The resistive value 209 may be a range of resistance values designated as $R_{5A}$, $R_{5B}$, $R_{5C}$, and $R_{5D}$. This range of resistive value 209 may be within, e.g., 1000-10,000 ohms. Each resistive channel 121, 123, 125, 127, 129 is dedicated to a different type of surgical instrument. As a result, depending on which resistive band is active, the digital controller 130 identifies the specific surgical instrument and determines (as well as adjusts) limits or functions of one or more parameters of the surgical instrument. In addition, because of the range of resistive values in each channel, multiple parameters may be set by a single set of resistance values. Thus, if a value is detected at $R_{1A}$ this may indicate a power setting, and a value at $R_{2A}$ may indicate a maximum time application setting. A value at $R_{3A}$ may indicate a maximum power setting, etc. Because of the broad ranges of resistive values available, a wide arrange of settings, and variables, as well as information about the microwave applicator 180, the other components of system 100, and the expected functionality of the microwave generator can be conveyed to the controller 130.

The use of this resistive ID scheme has a further effect in that it allows for the controller 130, which is removable from the microwave generator 110, to be switched to accommodate different types of or new generations of microwave applicators 180, remote temperature probes 190, and other components without having to take the microwave generator 110 out of service to perform software, firmware, or hardware upgrades.

The controller 130 may also be able to ascertain and retain information about all of the devices which are connected to the microwave generator 110. In this manner usage times of devices, such as the reusable cable 160, may be collected as monitored. Further, antiquated ablation probes 180 may be prevented from use, or even individual ablation probes 180 whose resistive ID information is already stored in an on-board memory on the controller 130 may be prevented from being re-used.

For example the reusable cable 160 and the microwave applicator 180 may both be disposable. The reusable cable 160 and the microwave applicator 180 may be used only once or may be used a predetermined number of times. A counter in the digital controller 130 may be associated with either the reusable cable 160 or the microwave applicator 180 or both. The counter may count the number of times the reusable cable 160 and/or the microwave applicator 180 having a specific resistive ID configuration has been used. After a predetermined number of uses, the counter may trigger an indicator (e.g., a visual or audible indicator) to prompt a user to replace the reusable cable and/or the microwave applicator. This and other data pertaining the use of the surgical system 100 and the components connected thereto may be stored locally in a memory in the digital controller, and may be downloaded to an external memory for later evaluation and analysis without departing from the scope of the present disclosure.

Moreover, three or more separate resistive values could be used in the device ID 170. The digital controller 130 would read all the values via the pass through and match them to a matrix identification to determine a device type and a manufacturer date. This increases the number of device IDs which could be used, and could also enable device use monitoring. If, for example, three readable elements were used in the device ID 170, each having 20 resistive value options (20×20×20 values–8000 unique combinations), as disposables are tracked in lots, this could allow for the digital controller 130 to limit the use of the expired lots.

Therefore, referring back to FIG. 1, once a connection has been established between the microwave applicator 180 and the microwave generator 110, the resistive identification connector 120 of the microwave generator 110 communicates directly with the device ID 170 of the microwave applicator 180 to identify the type of microwave applicator 180 connected to the microwave generator 110. This is accomplished by communicating resistance values incorporated in the device ID 170 and associated with the microwave applicator 180 directly to the resistive identification connector 120. For example, the device ID 170 may communicate various resistive values associated with the microwave applicator 180 that fall into the 10-100 ohm range. The resistive identification connector 120 corresponds such values with the second channel, e.g., channel 123 of the resistive identification connector 120. The second channel 123 of the resistive identification connector 120 corresponds to, e.g., a multi-mode microwave ablation applicator. Therefore, the resistive identification connector 120 conveys this information to the controller 130, which identifies the microwave applicator 180 as a multi-mode microwave ablation applicator.

Subsequently, once the match has occurred between the resistive values provided by the device ID 170 of the microwave applicator 180, the digital controller 130 is able to control the multi-mode microwave ablation applicator by adjusting one or more operations of the microwave generator 110. Thus, once the device ID 170 registers the microwave applicator 180 with the digital controller 130, the digital controller 130 is able to adjust functionality of the microwave generator 110 and the microwave applicator 180.

Therefore, the microwave generator 110 (which may be an existing off-the-shelf generator) can be provided with additional functionality, without the need of replacing the generator within the surgical system 100. The digital controller 130 acts as a smart peripheral device for enhancing the operations or functions provided by the existing microwave generator 110.

Another aspect of the present disclosure is the use of the radiometer 150. The radiometer 150 detects emissions from materials such as tissue, for example. The emissions detected by the radiometer 150 both before and after application of microwave energy can be sampled and converted to either an analog voltage or a digital signal and forwarded to the digital controller 130.

With this information, the digital controller 130 may change or alter or modify or adjust the energy delivered by the microwave generator 110 based on the tissue characteristics encountered by the microwave applicator 180. For example, when the tissue contacted by the microwave applicator 180 and sensed by the radiometer 150 is healthy tissue, the digital controller may prevent the microwave generator 110 from applying energy to the tissue. On the other hand, as the microwave applicator 180 approaches tumorous tissue, the digital controller 130 may prompt the microwave generator 110 to transmit energy to cauterize the tumorous tissue. The detection of the tumorous tissue (or healthy tissue) may be enabled by first transmitting from the microwave generator 110 through the microwave applicator 180 a non-therapeutic signal (e.g., very low power or duration) at the tissue in question and evaluating the emitted response to the interrogation. The digital controller can then employ algorithms and protocols to ascertain the type of tissue and present these results to the user via a connected display or an output on the microwave generator, or on the digital controller 130 itself.

Further, by continuing to detect the change in the radiometry reading during the application of energy, the digital controller 130 can make determinations regarding the cessation, or the sufficiency of the treatment of the tumorous tissue. The signals generated by the radiometer 150 permit the digital controller 130 to adjust operations of the microwave generator 110 based on the feedback received from the microwave applicator 180. The radiometry detector 150 enables radiometric detection of heating of the tissue by detecting electromagnetic waves of a frequency and signal strength emitted by the tissue indicating tissue temperature. Preferably the radiometry detector 150 operates at a frequency in the microwave range. The radiometry detector 150 is an optional component of the surgical system 100.

The radiometer 150 is in electrical communication with a voltage to frequency converter 114 (see FIG. 1). The voltage to frequency converter 114 may enable the digital controller 130 to receive either an analog voltage or a digital representative of the emissions received by the radiometer 150. Digital representation of the radiometer output has advances common to digital signal communications, including but not limited to enhanced bandwidth and noise immunity.

With combined use of the digital controller 130 and radiometer measurement of the tissue state about the ablation probe, the system could dynamically avoid certain unwanted physiological responses which occur during rapid heating, such as the rapid phase change of physiological fluids from liquid to gas. The controller 130 would in this case avoid exceeding 100 dC as measured by the radiometer by pulsing/reducing microwave power to the probe. Other dynamic control of the ablation progression is envisioned and not limited to this example.

According to a further embodiment of the present disclosure, information communicated by the device ID 170 of the microwave applicator 180 may be directly sent to the digital controller 130 via a digital pass-through line 195 to allow direct communication between the microwave applicator 180 (or other components of the system 100) and the digital controller 130. The at least one digital pass-through line 195 includes electrical isolation. Therefore, even in instances where the microwave generator 110 does not use any programmable logic and there is no computer processing conducted within the microwave generator 110, the use of the digital pass-through line 195 allows for all digital communications between the microwave applicator 180 (or other components of the system 100) and the digital controller 130.

Figure 3:
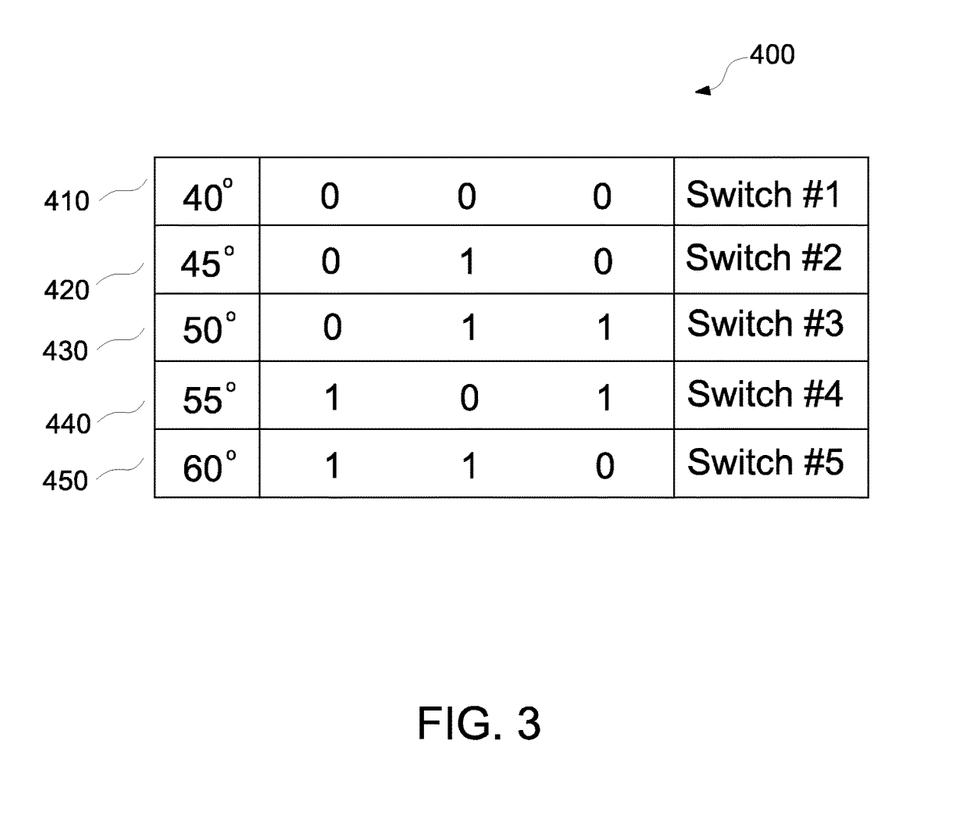
FIG. 3 depicts a plurality of dip switches configured to allow for high temperature cutoff selectability, in accordance with an embodiment of the present disclosure.

FIG. 3 depicts a plurality of dip switches configured to allow for high temperature cutoff selectability, in accordance with an embodiment of the present disclosure.

The dip switch configuration 400 depicts five dip switch configurations for three dip switches, each associated with a different temperature (or temperature range). Of course, one skilled in the art may contemplate a different number of dip switches each associated with a different temperature or temperature range. For example, in this exemplary embodiment, the first dip switch configuration 410 may represent a shut-off temperature of 40° degrees, the second dip switch configuration 420 may represent a shut-off temperature of 45° degrees, the third dip switch configuration 430 may represent a shut-off temperature of 50° degrees, the fourth dip switch configuration 440 may represent a shut-off temperature of 55° degrees, and the fifth dip switch configuration 450 may represent a shut-off temperature of 60° degrees. The temperature shut-off for each dip switch configuration 410, 420, 430, 440, 450 may be represented in binary form, as illustrated in FIG. 3. Therefore, a user is permitted to manually select a shut-off temperature related to the microwave applicator 180 (see FIG. 1) to be sensed by the remote temperature probe 190. When the selected dip switch configuration temperature is sensed by the remote temperature probe, the microwave generator 110 can be automatically shut-off and prevented from providing additional energy to the microwave applicator 180 based on a tissue temperature measured at the surgical site. This may be performed via analog circuitry within the microwave generator 110, or by sending a signal to the digital controller 130 which itself generates a control signal shutting off the generator.

The features and aspects of the present disclosure may be implemented in surgical system 100 in any suitable fashion, e.g., via the hardware and software configuration of surgical system 100 or using any other suitable software, firmware, and/or hardware.

For instance, when implemented via executable instructions, various elements of the present disclosure are in essence the code defining the operations of such various elements. The executable instructions or code may be obtained from a readable medium (e.g., a hard drive media, optical media, EPROM, EEPROM, tape media, cartridge media, flash memory, ROM, memory stick, and/or the like) or communicated via a data signal from a communication medium (e.g., the Internet). In fact, readable media may include any medium that may store or transfer information.

The computer means or computing means or processing means may be operatively associated with the assembly, and is directed by software to compare the first output signal with a first control image and the second output signal with a second control image. The software further directs the computer to produce diagnostic output. Further, a means for transmitting the diagnostic output to an operator of the verification device is included. Thus, many applications of the present disclosure could be formulated. The exemplary network disclosed herein may include any system for exchanging data or transacting business, such as the Internet, an intranet, an extranet, WAN (wide area network), LAN (local area network), satellite communications, and/or the like. It is noted that the network may be implemented as other types of networks.

Additionally, "code" as used herein, or "program" as used herein, may be any plurality of binary values or any executable, interpreted or compiled code which may be used by a computer or execution device to perform a task. This code or program may be written in any one of several known computer languages. A "computer," as used herein, may mean any device which stores, processes, routes, manipulates, or performs like operation on data. A "computer" may be incorporated within one or more transponder recognition and collection systems or servers to operate one or more processors to run the transponder recognition algorithms. Moreover, computer-executable instructions include, for example, instructions and data which cause a general purpose computer, special purpose computer, or special purpose processing device to perform a certain function or group of functions. Computer-executable instructions also include program modules that may be executed by computers in stand-alone or network environments. Generally, program modules include routines, programs, objects, components, and data structures, etc. that perform particular tasks or implement particular abstract data types.

Though the digital controller 130 is generally described herein as automatically controlling or adjusting or operating one or more functions of the microwave generator 110, it is understood that that a user may also manually adjust one or more operations of the microwave generator 110.

Concerning the exemplary embodiments of the present disclosure, the microwave applicator may be a rigid applicator or a flexible applicator. One skilled in the art may contemplate using any type of applicator.

This description may use the phrases "in an embodiment," "in embodiments," "in some embodiments," or "in other embodiments," which may each refer to one or more of the same or different embodiments in accordance with the present disclosure.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as, for example, microwave ablation, radiofrequency (RF) ablation, or microwave or RF ablation-assisted resection.

As it is used in this description, "energy applicator" generally refers to any device that can be used to transfer energy from a power generating source, such as a microwave or RF electrosurgical generator, to tissue. For the purposes of the present disclosure, the term "energy applicator" is interchangeable with the term "energy-delivery device." As it is used in this description, "transmission line" generally refers to any transmission medium that can be used for the propagation of signals from one point to another.

As it is used in this description, the term "controller" refers to any electrical device that employs digital and/or analog components to generate digital and/or analog signals to control or drive another device. The term "controller" may refer to a digital signal processor, a microcontroller, or a computer having a processor, a memory, and input/output ports for carrying out some of the methods described herein.

The word "exemplary" is used herein to mean "serving as an example, instance, or illustration." Any embodiment described herein as "exemplary" is not necessarily to be construed as preferred or advantageous over other embodiments. The word "example" may be used interchangeably with the term "exemplary."

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure.

The foregoing examples illustrate various aspects of the present disclosure and practice of the methods of the present disclosure. The examples are not intended to provide an exhaustive description of the many different embodiments of the present disclosure. Thus, although the foregoing present disclosure has been described in some detail by way of illustration and example for purposes of clarity and understanding, those of ordinary skill in the art will realize readily that many changes and modifications may be made thereto without departing form the spirit or scope of the present disclosure.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

The invention claimed is:

1. A surgical system comprising:
   a microwave generator including a resistive identification connector having a plurality of resistive channels, each resistive channel having a plurality of resistive values;
   a microwave applicator having a device identifier, the device identifier including resistive information for identifying the microwave applicator, the microwave applicator configured to be connected to the microwave generator via a reusable cable; and
   a digital controller configured to be connected to the resistive identification connector of the microwave generator,
   wherein the resistive information of the microwave applicator is relayed to the digital controller via one of the plurality of resistive channels of the resistive identification connector to enable the digital controller to control the microwave applicator by adjusting at least one operation of the microwave generator, and wherein the resistive channel is selected in order to match the resistive information and identify the microwave applicator.

2. The surgical system according to claim 1, wherein the resistive information is associated with parameters of the microwave applicator, the parameters including at least one of a power limit, a time limit, a temperature limit, and a reflected power limit of the microwave applicator.

3. The surgical system according to claim 1, wherein the plurality of resistive channels are five channels, each of the five channels configured to correspond to a different microwave applicator connected to the microwave generator.

4. The surgical system according to claim 1, wherein a radiometry detector is connected between the microwave generator and the reusable cable.

5. The surgical system according to claim 4, wherein the radiometry detector senses emissions from tissue in proximity of the microwave applicator.

6. The surgical system according to claim 1, wherein a footswitch is connected to the microwave generator.

7. The surgical system according to claim 1, wherein a remote temperature probe is connected to the microwave generator.

8. The surgical system according to claim 1, wherein a plurality of dip switches are incorporated onto the microwave generator, the plurality of dip switches configured to allow for high temperature cutoff selectability.

9. The surgical system according to claim 1, wherein the digital controller reads information stored in the device identifier of the microwave applicator to continuously, and in real-time, adjust the at least one operation of the microwave generator.

10. The surgical system according to claim 1, wherein the microwave generator includes at least one digital pass-through line to allow direct communication between the microwave applicator and the digital controller.

* * * * *

UNITED STATES PATENT AND TRADEMARK OFFICE
CERTIFICATE OF CORRECTION

PATENT NO. : 10,085,801 B2  
APPLICATION NO. : 14/805084  
DATED : October 2, 2018  
INVENTOR(S) : Brannan Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 492 days.

Signed and Sealed this  
Twenty-third Day of April, 2019

Andrei Iancu  
*Director of the United States Patent and Trademark Office*